United States Patent [19]

Frenkel

[11] Patent Number: 5,005,577
[45] Date of Patent: Apr. 9, 1991

[54] INTRAOCULAR LENS PRESSURE MONITORING DEVICE

[76] Inventor: Ronald E. P. Frenkel, 1501 Beacon St., No. 202, Brookline, Mass. 02146

[21] Appl. No.: 235,321

[22] Filed: Aug. 23, 1988

[51] Int. Cl.$^5$ ................................................ A61B 3/16
[52] U.S. Cl. .................................... 128/645; 128/652; 128/748
[58] Field of Search .................. 128/748, 645–652, 128/631, 903; 623/6

[56] References Cited
U.S. PATENT DOCUMENTS 4,089,329  5/1978  Couvillon ............................ 128/652
4,305,399 12/1981  Beale ................................ 128/748 X

OTHER PUBLICATIONS

Linden et al., Abstract Development of a Micromachined Transensor for Monitoring of Intraocular Pressure in 1988 World Congress on Medical Physics and Biomedical Engineering, San Antonio, Texas, p. 367.

Primary Examiner—Max Hindenburg
Assistant Examiner—J. P. Lacyk
Attorney, Agent, or Firm—Choate, Hall & Stewart

[57] ABSTRACT

An apparatus for monitoring intraocular pressure including an implantable intraocular lens and at least one sensor apparatus responsive to intraocular pressure being affixed to the lens.

10 Claims, 2 Drawing Sheets

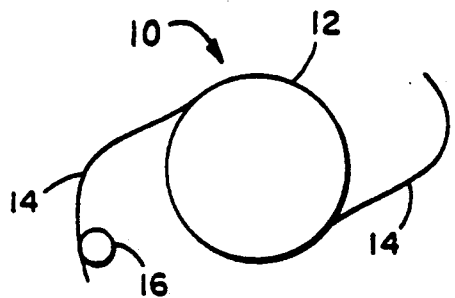
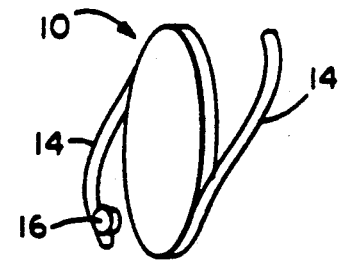
FIG. 1a  FIG. 1b
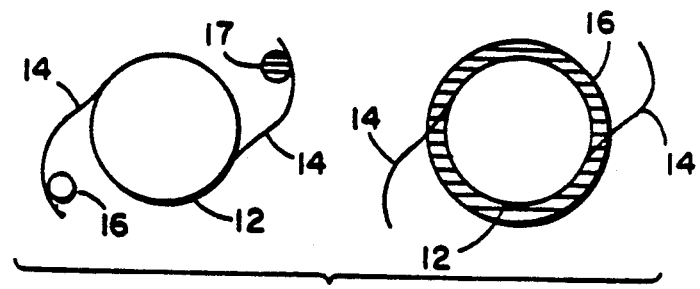
FIG. 1d
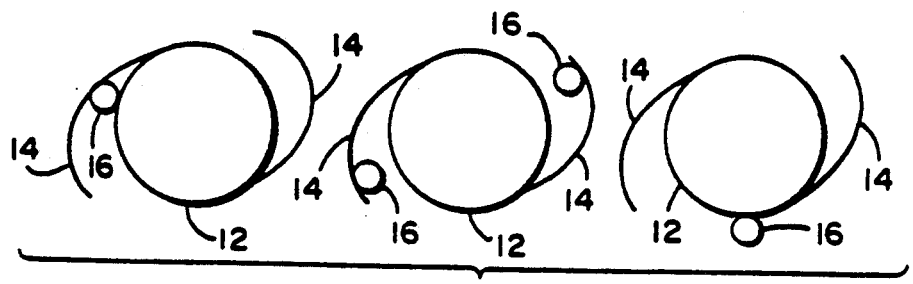
FIG. 1c
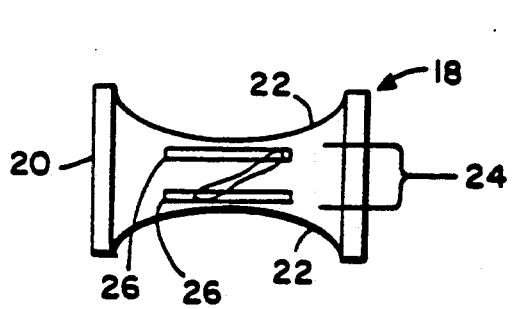
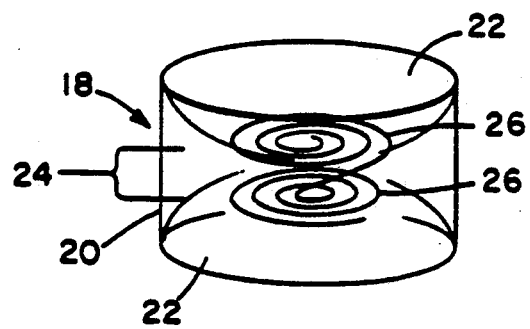
FIG. 2a (PRIOR ART)  FIG. 2b (PRIOR ART)

INTRAOCULAR LENS PRESSURE MONITORING DEVICE

BACKGROUND OF THE INVENTION

This invention relates to an apparatus and method for in situ monitoring of intraocular pressure.

The human eye contains a flexible transparent structure called the crystalline lens. The function of this structure is to focus light passing through the cornea and pupil onto the photoreceptors which form the retina Although it is termed the crystalline lens, it is composed of living tissue. Cells of the lens are arranged into fibers and it is the precise orientation of groups of these fibers which imparts to the lens its flexibility while maintaining its transparency.

In certain diseases, the arrangement of fibers in the lens becomes disrupted. When this occurs, those regions which are disrupted lose their transparency and become opaque. An opacity is termed a cataract. If a cataract involves a substantial portion of the lens, vision may become impaired. In these cases, it may be necessary to remove the lens surgically and replace it with a lens of synthetic material in order to return sight to the patient.

One of the disease conditions which can lead to cataract formation is an increase in intraocular pressure known as glaucoma. In addition to damaging the lens, an increase in intraocular pressure can damage the neural portions of the eye and lead to permanent blindness. It is possible to treat glaucoma either with drugs or surgery, but to do so successfully, it is necessary to monitor the pressure within the eye.

Typically, an ophthalmologist will measure the pressure within the eye with a tonometer. (See: Textbook of Glaucoma, M. B. Shields, Williams and Wilkins, Pub., 2nd ed, 1987 Chapt. 3, Pg. 54-55) The cornea is topically anesthetized and the tonometer probe is used to flatten cornea. The amount of pressure required to flatten the cornea to a specified amount is a function of the internal pressure in the eye. The difficulty arises that the pressure measurement so obtained is valid only for the instant the measurement was taken. Frequently repeated or continuous measurements are not feasible using this method, and an in situ device is required to monitor intraocular pressure continuously.

Some 20 years ago passive miniature endoradiosondes were developed to measure the Pressure within the eye. (cf. Miniature Passive Pressure Transensor for Implanting in the Eye, C. C. Collins, IEEE Transactions on Bio-medical Engineering, April 1967, p. 74 which is herein incorporated by reference and Intraocular Pressure Transensor Fabrication, C. C. Collins, is herein incorporated by reference) These devices are small enough to be inserted into the eye.

The device is a resonant circuit whose resonance frequency is dependent upon the pressure on the circuit. Therefore, as the pressure within the eye changes, the resonance frequency of the device changes. If the eye and its endoradiosonde are exposed to an electromagnetic field of variable frequency, absorption of energy from the field will occur when the frequency of the field matches the resonance frequency of the endoradiosonde. Therefore, by measuring this frequency, the intraocular pressure of the eye can be determined.

While this technique has been used to measure the intraocular pressure in laboratory animals, it has not been used in humans. The reason for this is that intraocular surgery is a serious procedure which cannot be justified for the implantation of a purely diagnostic device. Further, presence of a free floating sensor in the eye could itself result in further damage to the structures of the eye.

What is required then, is for the sensor to be attached within the eye in such a way that it would not damage the tissues of the eye. Glaucoma patients who require lens removal provide the ideal set of circumstances for the in situ continuous monitoring of intraocular pressure because the device can be placed at or near where the eye's crystalline lens normally would reside.

SUMMARY OF THE INVENTION

The invention disclosed herein involves the attachment of a pressure sensor to an implantable intraocular lens so that, following lens replacement surgery, the intraocular pressure may be monitored continuously and in situ.

In one embodiment, the pressure transducer is a resonant circuit. In particular, the configuration is a cylinder, closed at each end by a diaphragm. The geometry of the circuit is changed as pressure forces the diaphragms into the cylinder, and this change in geometry manifests itself as a change in resonance frequency of the circuit.

The present invention enables the in situ monitoring on a continuous basis of intraocular pressure using the same operation in which the diseased lens is replaced. Further, since the sensor and lens is a single unit, the possibility of further damage to the eye by the sensor is essentially eliminated.

Description of the Preferred Embodiments

The drawing is briefly described as follows.

FIG. 1(a) is a plan view of an embodiment the invention consisting of the implantable lens and attached sensor. FIG. 1(b) is a perspective view of the embodiment of FIG. 1(a). FIG. 1(c) is a plan view of an embodiment of the invention indicating several possible positions of the sensors. FIG. 1(d) are plan views of an embodiment of the invention wherein the sensor surrounds the periphery of the optic and embodiment of the invention in which the sensor is counter balanced by a counter mass.

FIG. 2(b) is a perspective view or a passive endoradiosonde known to the art. FIG. 2(a) is a cross-sectional view of the endoradiosonde of FIG. 2(b).

Figure 3:
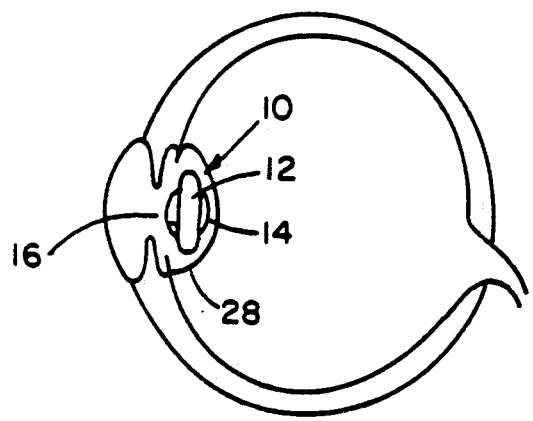
FIG. 3 is a view of the embodiment of FIG. 1(a) implanted within the eye.

A typical replacement lens 10 is shown in FIGS. 1a and 1b and consists of a transparent central portion 12, the optic, which is the actual lens, and two or more structural elements 14, the haptics, which position the optic 12 within the eye. A pressure sensor 16 is shown located on one of the haptics 14. It should be appreciated that the location of the sensor 16 shown on the haptic 14 is illustrative only, as shown in FIG. 1a, and that the sensor 16 could be located anywhere on the haptic 14 or periphery of the optic 12, and that more than one sensor 16 could be mounted (FIG. 1c). Further, it should be noted that a lens 10, may be constructed without haptics 14, and therefore, in that case, the sensor 16, would only be attached to the optic 12. Additionally, the lens 10, could be so constructed that the sensor 16 encompassed the entire periphery of the lens 10 (FIG. 1d). The only restriction is that the sensor 16 not be positioned so as to interfer with the Passage of light through the optic 12. It might be determined, that as well as multiple sensors 16, it is necessary to counter balance the sensor 16 with a counter weight 17 of the same mass as the sensor 16 (FIG. 1(d)). Such a determination is within the capabilities of one skilled in the art.

To make a Pressure sensor small enough-to be placed within the eye it may be preferable to make the device passive, so as not to require an in situ power source. A further advantage of having a passive device implanted in the eye is that such a device will have a longer useful life since the replacement of a power source would require additional surgery and so not be feasible.

FIGS. 2a and 2b show a typical passive endoradiosonde 18 comprising a non-conducting cylinder 20, which is sealed on each end by diaphragms 22. A resonant circuit 24 consists of a connected pair of spaced apart archimedean-spiral coils 26 which lie parallel to each other, and each of which is attached to a separate one of the diaphragms 22. As the pressure on the diaphragms 22 increases, the diaphragms 22 are forced into the cylinder 20 and the spiral coils 26 are forced into closer proximity. This change in separation alters their resonant frequency of the circuit 24. By measuring the resonant frequency, the pressure may be determined.

FIG. 3 shows the placement within the eye lens/sensor 10 combination of the invention. Normally during lens replacement surgery the natural lens is removed, but its surrounding supporting structure, a posterior capsule 28, is not. The replacement lens 10 is then placed within the capsule 28. The haptics 14 position the optic 12 in the center of the capsule 28. The sensor 16, shown attached to the haptic 14 is exposed to pressure within the eye. The lens sensor may also be placed just behind or in front of the iris; where ever the surgeon finds it necessary to place the lens.

Figure 4:
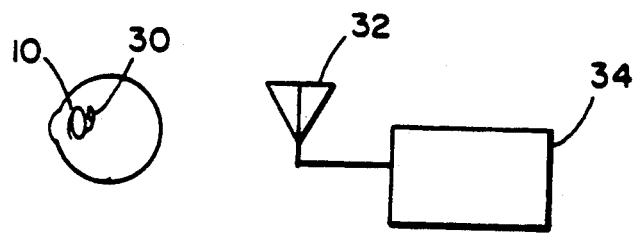
FIG. 4 is a schematic illustration of a generalized system for monitoring intraocular Pressure.

It is not required that the pressure sensor of the invention be passive. Conceivably technology will progress to the point where a power supply and transmitter responsive to pressure will be small enough to be implanted in the eye. Such a device could include a photoelectric cell to generate the required power from a portion of the light entering the eye. FIG. 4 depicts a system for measuring intraocular pressure in the case of an active transmitter. In this embodiment an active sensor 30 is implanted in the eye. An antenna 32 is located extracorporeally but sufficiently near the eye so as to receive transmissions from the active sensor 30. These transmissions are received and decoded by a receiver 34.

Figure 5:
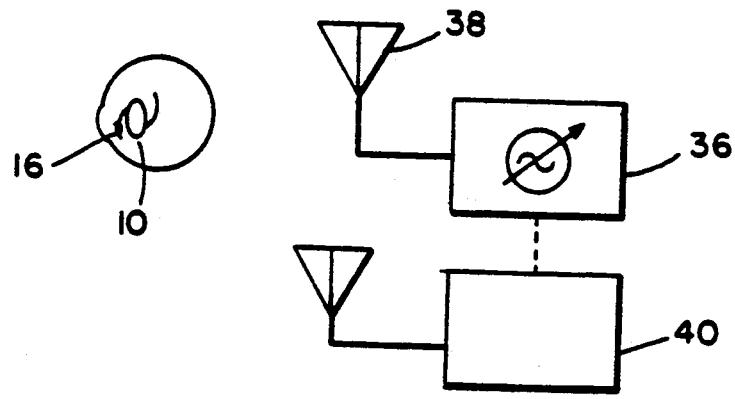
FIG. 5 is a schematic illustration of a system for monitoring intraocular pressure utilizing a sensor which comprises, in part, a passive endoradiosonde, as in FIG. 2.

FIG. 5 depicts the system for monitoring intraocular pressure for the passive sensor 16 as shown in FIG. 2. Again the passive endoradiosonde or sensor 16 is implanted within the eye. A variable frequency radio transmitter 36 sweeps through the appropriate frequencies and broadcasts these frequencies through a transmitting antenna 38. At the same time, a grid-dip meter 40 is measuring the amount of energy in the field being generated by transmitter 36. When the resonant frequency of the endoradiosonde 16 is matched to the frequency being transmitted by the variable frequency transmitter 36, the endoradiosonde 16 will begin to absorb energy from the electromagnetic field and this will be detected by the grid-dip meter 40, thereby determining the resonant frequency and the pressure within the eye.

Having shown the preferred embodiment, those skilled in the art will realize many variations are possible which will still be within the scope and spirit of the claimed invention. Therefore, it is the intention to limit the invention only as indicated by the scope of the claims.

What is claimed is:

1. An apparatus for monitoring intraocular pressure comprising an intraocular lens implantable within the eyeball and at least one sensor apparatus affixed to said implantable intraocular lens and implantable therewith within the eyeball, said sensor apparatus being responsive to intraocular pressure.

2. A system for monitoring intraocular pressure comprising:

an intraocular lens implantable within the eyeball and an intraocular pressure sensor affixed to said intraocular lens and implantable therewith within the eyeball, said intraocular pressure sensor being responsive to intraocular pressure, and an extracorporeal device responsive to the intraocular pressure on the implantable intraocular pressure sensor.

3. The apparatus of claim 2 wherein said passive endoradiosonde comprises a resonant circuit whose resonant frequency is responsive to intraocular pressure.

4. The apparatus of claim 3 wherein said resonance circuit comprises a pair of parallel, coaxial, spaced apart archimedean spiral coils.

5. The apparatus of in claim 4 wherein each coil is located within a nonconducting cylinder and is attached to an interior surface of one of each of two nonconducting diaphragms which seal each end of the nonconducting cylinder.

6. The apparatus of claim 1 wherein the lens further comprises an optic and at least 1 haptic and the sensor is affixed to a haptic of the lens.

7. The apparatus of claim 1 wherein the lens further comprises an optic and the sensor is affixed to the optic of the lens.

8. A system for monitoring intraocular pressure comprising:

an implantable intraocular lens and an implantable intraocular pressure sensor affixed thereto responsive to intraocular pressure and an extracorporeal device responsive to the intraocular pressure on the implantable intraocular pressure sensor.

9. The system of claim 8 wherein the implantable intraocular pressure sensor is a passive endoradiosonde.

10. The system of claim 9 wherein the extracorporeal device is a sweeping variable frequency grid-dip meter for determining the resonant frequency of the endoradiosonde.

* * * * *

UNITED STATES PATENT AND TRADEMARK OFFICE
CERTIFICATE OF CORRECTION

PATENT NO. : 5,005,577
DATED : April 9, 1991
INVENTOR(S) : Ronald E. P. Frenkel

It is certified that error appears in the above-identified patent and that said Letters Patent is hereby corrected as shown below:

Column 1, line 12: change "tina Although" to -- tina. Although --.

Column 1, line 47: change "Pressure" to -- pressure --.

Column 2, line 43: change "and embodiment" to -- and an embodiment --.
           line 46: change "or" to -- of --.
           line 52: change "Pressure" to -- pressure --.

Column 3, line 6: change "Passage" to -- passage --.
           line 12: change "Pressure" to -- pressure --.
           line 12: change "enough-to" to -- enough to --.

Signed and Sealed this

Eleventh Day of August, 1992

Attest:

DOUGLAS B. COMER

*Attesting Officer*      *Acting Commissioner of Patents and Trademarks*